(12) United States Patent
Kolp et al.

(10) Patent No.: US 7,307,717 B2
(45) Date of Patent: Dec. 11, 2007

(54) OPTICAL FLOW CELL CAPABLE OF USE IN HIGH TEMPERATURE AND HIGH PRESSURE ENVIRONMENT

(75) Inventors: Joseph P. Kolp, North Canton, OH (US); Thomas J. Sebok, Tallmadge, OH (US); Mark J. Brodecky, Uniontown, OH (US)

(73) Assignee: Lockheed Martin Corporation, Akron, OH (US)

( * ) Notice: Subject to any disclaimer, the term of this patent is extended or adjusted under 35 U.S.C. 154(b) by 165 days.

(21) Appl. No.: 11/228,172

(22) Filed: Sep. 16, 2005

(65) Prior Publication Data

US 2007/0064226 A1 Mar. 22, 2007

(51) Int. Cl.
*G01N 1/10* (2006.01)

(52) U.S. Cl. .................................. 356/246; 356/70

(58) Field of Classification Search ................ 356/244, 356/266, 70
See application file for complete search history.

(56) References Cited

U.S. PATENT DOCUMENTS

| | | | |
|---|---|---|---|
| 3,198,064 A | 8/1965 | Moore | 88/14 |
| 3,886,264 A | 5/1975 | Walker et al. | 250/343 |
| 3,947,121 A | 3/1976 | Cotter et al. | 356/38 |
| 4,393,466 A | 7/1983 | Deindoerfer et al. | 364/415 |
| 4,582,684 A | 4/1986 | Vogel et al. | 422/57 |
| 4,804,267 A | 2/1989 | Greenfield | 356/335 |
| 4,807,267 A | 2/1989 | Rifu et al. | 378/7 |
| 4,872,753 A * | 10/1989 | Danigel et al. | 356/246 |
| 5,030,421 A | 7/1991 | Muller | 422/102 |
| 5,046,854 A * | 9/1991 | Weller et al. | 356/440 |
| 5,098,661 A | 3/1992 | Frohelich et al. | 422/102 |
| 5,241,189 A | 8/1993 | Vandagriff et al. | 250/575 |
| 5,572,320 A | 11/1996 | Reintjes et al. | 356/335 |
| 5,594,544 A | 1/1997 | Horiuchi et al. | 356/73 |
| 5,766,957 A | 6/1998 | Robinson et al. | 436/165 |
| 5,883,721 A | 3/1999 | Gilby et al. | 356/440 |
| 6,069,694 A * | 5/2000 | VonBargen | 356/246 |
| 6,104,483 A | 8/2000 | Sebok et al. | 356/244 |
| 6,290,912 B1 | 9/2001 | Doms | 422/82.05 |
| 6,587,195 B1 * | 7/2003 | Jennings | 356/246 |
| 2003/0030810 A1 | 2/2003 | Sebok et al. | 356/436 |

(Continued)

FOREIGN PATENT DOCUMENTS

DE 198 59 479 A1 12/1999

(Continued)

*Primary Examiner*—Tarifur Chowdhury
*Assistant Examiner*—Jonathon D Cook
(74) *Attorney, Agent, or Firm*—Renner Kenner Greive Bobak Taylor & Weber

(57) ABSTRACT

An optical flow cell is disclosed that includes a flow cell body having an inlet and an outlet with a flow opening therebetween to allow a fluid to pass therethrough. A light entry fixture and a light imaging fixture are transversely carried by the flow cell body to allow viewing of the flow opening, wherein the light entry fixture is positioned at one side of the body and the light imaging fixture is positioned at an opposite side of the body. The fixtures are made from at least some materials different than then flow cell body but having a thermal rate of expansion that matches a thermal rate of the body so as to maintain a predetermined size of the flow opening during temperature fluctuations.

10 Claims, 8 Drawing Sheets

U.S. PATENT DOCUMENTS

| | | | |
|---|---|---|---|
| 2004/0001200 A1* | 1/2004 | Hirakawa et al. | 356/244 |
| 2004/0027568 A1* | 2/2004 | Maiefski et al. | 356/326 |
| 2004/0189988 A1* | 9/2004 | Scaduto | 356/244 |
| 2006/0044554 A1* | 3/2006 | Mertz et al. | 356/246 |

FOREIGN PATENT DOCUMENTS

| | | |
|---|---|---|
| EP | 0 300 965 A1 | 1/1989 |
| EP | 0 302 009 A | 2/1989 |
| EP | 0507746 | 10/1992 |
| EP | 507746 A2 * | 10/1992 |
| EP | 0 556 971 A3 | 2/1993 |
| EP | 0 644 414 A3 | 8/1994 |
| EP | 1 245 945 A2 | 3/2002 |
| EP | 1 406 079 A2 | 4/2004 |
| GB | 2 116 704 A | 1/1979 |
| JP | 62-112034 | 5/1987 |
| JP | 7-218417 | 8/1995 |
| WO | WO 95/12118 | 5/1995 |

* cited by examiner

OPTICAL FLOW CELL CAPABLE OF USE IN HIGH TEMPERATURE AND HIGH PRESSURE ENVIRONMENT

TECHNICAL FIELD

The present invention relates generally to fluid inspection systems. More specifically, the invention relates to an optical flow call used in fluid inspection systems that retains its integrity at high pressures and high temperatures.

BACKGROUND ART

Generally, three factors contribute to engine oil contamination: by-products given off by combustion, debris entering through an engine's air intake, and metal shavings created by engine wear. In particular, these metal shavings (on the order of 100 microns or less) are indicative of the health of the machine. The physical characteristics (e.g., size and shape) of these metal shavings and other observed debris may contain information relating to the real-time health of the machine.

In today's marketplace, automotive manufacturers have developed numerous systems for inferring whether a user needs to change engine oil or other automotive fluids. An example of such a system is an onboard monitoring system in most automobiles that tracks several variables including engine running time, vehicle mileage, and temperature. Based on this information, an onboard computer calculates when the engine oil should be changed and, in turn, lights the oil lamp indicator on the vehicle's dashboard. While this and other similar systems may notify automobile owners of oil change deadlines, these systems lack the capacity to directly detect if metal shavings or other contaminants exist in the engine oil and are unable to determine the real-time health of the machine.

In light of this shortcoming, systems that directly analyze fluid were developed. The traditional method for directly analyzing a fluid was to extract an oil sample from a disengaged engine, and then to send the oil to a laboratory for testing. Although necessary for safety, this process was time consuming.

More recently, systems utilizing optical near-field imaging techniques have been developed. These systems generally consist of a light source, a light detection device, a flow cell, and a pump or other means to deliver the fluid to the flow cell. One such system, the optical near-field imaging system disclosed in U.S. Pat. No. 6,104,483, incorporated herein by reference, determines the number of particles in the fluid, then tabulates each particle's size and physical characteristics. The physical characteristics of a particle directly correspond to a particular wear mechanism. Thus, in undergoing an analysis of engine oil, this system can correlate the tabulated information with a specific wear mechanism (e.g., metal shavings created by engine wear or debris entering through an engine's intake). Ultimately, the system could inform a user to the source of the particles, thereby enabling the user to diagnose and remedy any problems that may exist.

While these optical near-field imaging systems show promise in making real-time diagnoses of machines, current systems have a major shortcoming, namely, they cannot withstand the stresses associated with the high pressures or high temperatures present in an engine or similar environment. In this type of environment, pressures may routinely reach 5000 psi and temperatures may reach 140° C. Accordingly, systems utilizing optical near-field imaging techniques have not been successfully incorporated into these environments.

While known flow cells are sufficient in their stated purpose, these devices are not built to withstand the high pressure and high temperatures that exist when a device is mounted directly in an engine or similar environment. Therefore, the need exists for a flow cell that can withstand high pressures and high temperatures, while still obtaining accurate measurements and images.

DISCLOSURE OF THE INVENTION

In general, the present concept relates to an optical flow cell capable of use in high temperature and high pressure environment.

It is an aspect of the present invention to provide an optical flow cell comprising a flow cell body having an inlet and an outlet with a flow opening therebetween to allow a fluid to pass therethrough, the flow cell body having a thermal expansion rate and a light entry fixture and a light imaging fixture carried by the flow cell body, the light entry fixture positioned at one side of the flow opening and the light imaging fixture positioned at an opposite side of the flow opening, the fixtures made from at least some materials different than the flow cell body but having the thermal expansion rate so as to maintain a predetermined size of the flow opening.

BRIEF DESCRIPTION OF THE DRAWINGS

For a complete understanding of the objects, techniques and structure of the invention, reference should be made to the following detailed description and accompanying drawings wherein.

BEST MODE FOR CARRYING OUT THE INVENTION

Figure 1:
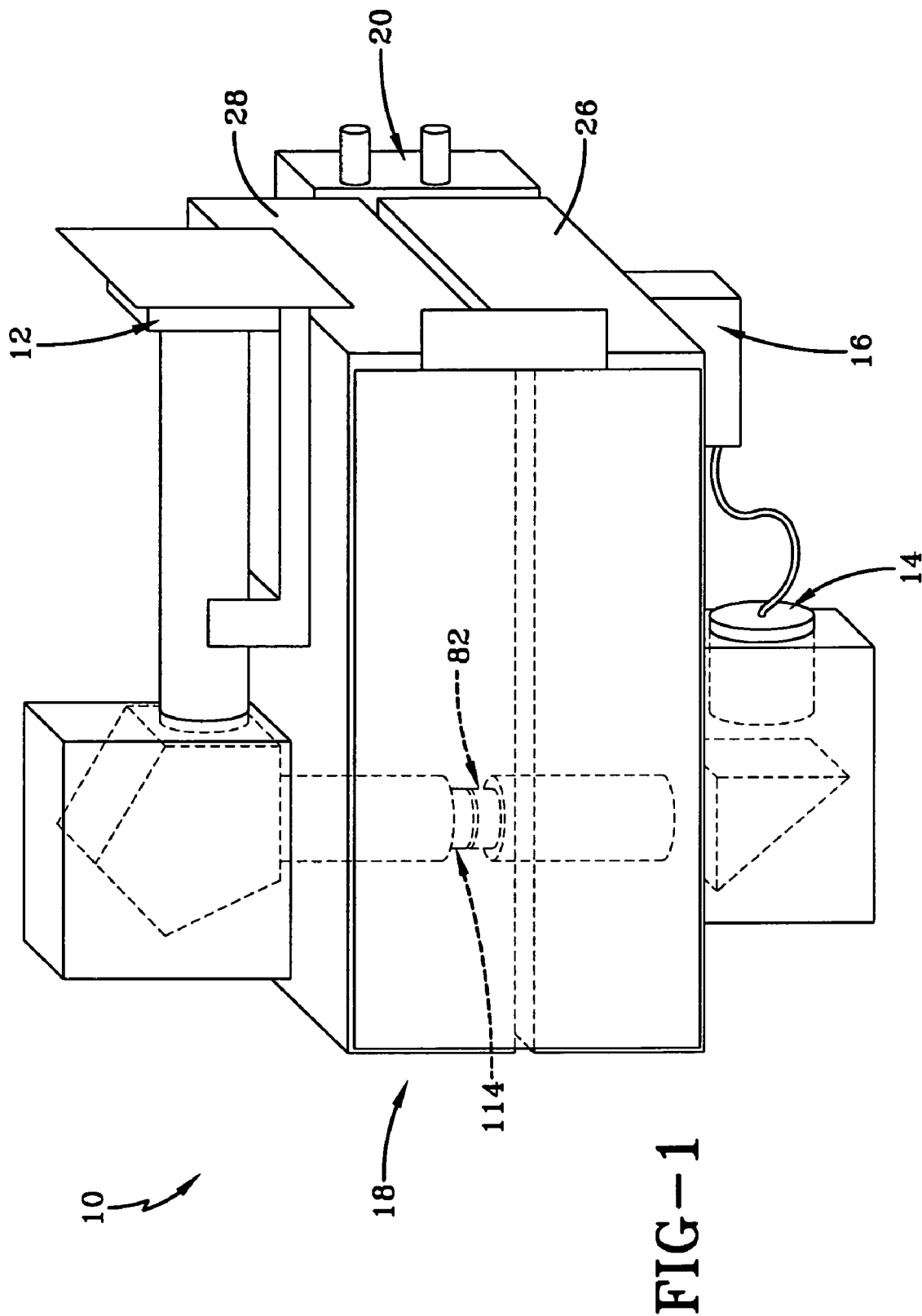
FIG. 1 is a perspective schematic drawing of a near-field optical imaging system according to the concepts of the present invention.

Referring now to the drawings, it can be seen that FIG. 1 shows an optical near-field imaging system designated generally by the numeral 10. The system 10 generally includes a detection and analysis device 12, a light collimator 14, a light source 16, an optical flow cell 18, and a flow delivery apparatus 20. This system 10 is just one embodiment of the present concept and does not limit the scope of the claims in any way.

The light source 16 is likely a laser or some other form of device that generates a collimated light beam. The light detection and analysis device 12 is positioned to receive the beam generated by the light source 16 and may include such detection components as a photo-detector, CMOS image array, or other device that is capable of performing imaging functions. The analysis component of the device 12 is coupled to the light detection component and analyzes the light received. The analysis component is most likely a microprocessor, general purpose CPU, DSP, FPGA, ASIC, or other similar device that is compatible with the light detection device. The optical flow cell 18 is interposed substantially between the light source 16 and the detection and analysis device 12. The optical flow cell 18 facilitates the flow of a fluid (e.g., engine oil) to enable optimum operation of the light source 16 and the detection and analysis device 12. The system 10 also includes a flow delivery apparatus 20 for delivering the liquid to the flow cell 18. This flow delivery apparatus 20 may be a pump, a channel, or some other mechanism for delivering a fluid through the flow cell 18. The flow delivery apparatus 20 may be connected to a piece of operating equipment. Thus, the system may be used with an engine or other piece of machinery while the machinery is operating. In other words, the system 10 can analyze and monitor the fluid in real-time as it is used by the machinery.

With this brief overview of the system in mind, particular embodiments for an optical flow cell 18 are discussed in further detail in the following paragraphs.

Figure 2:
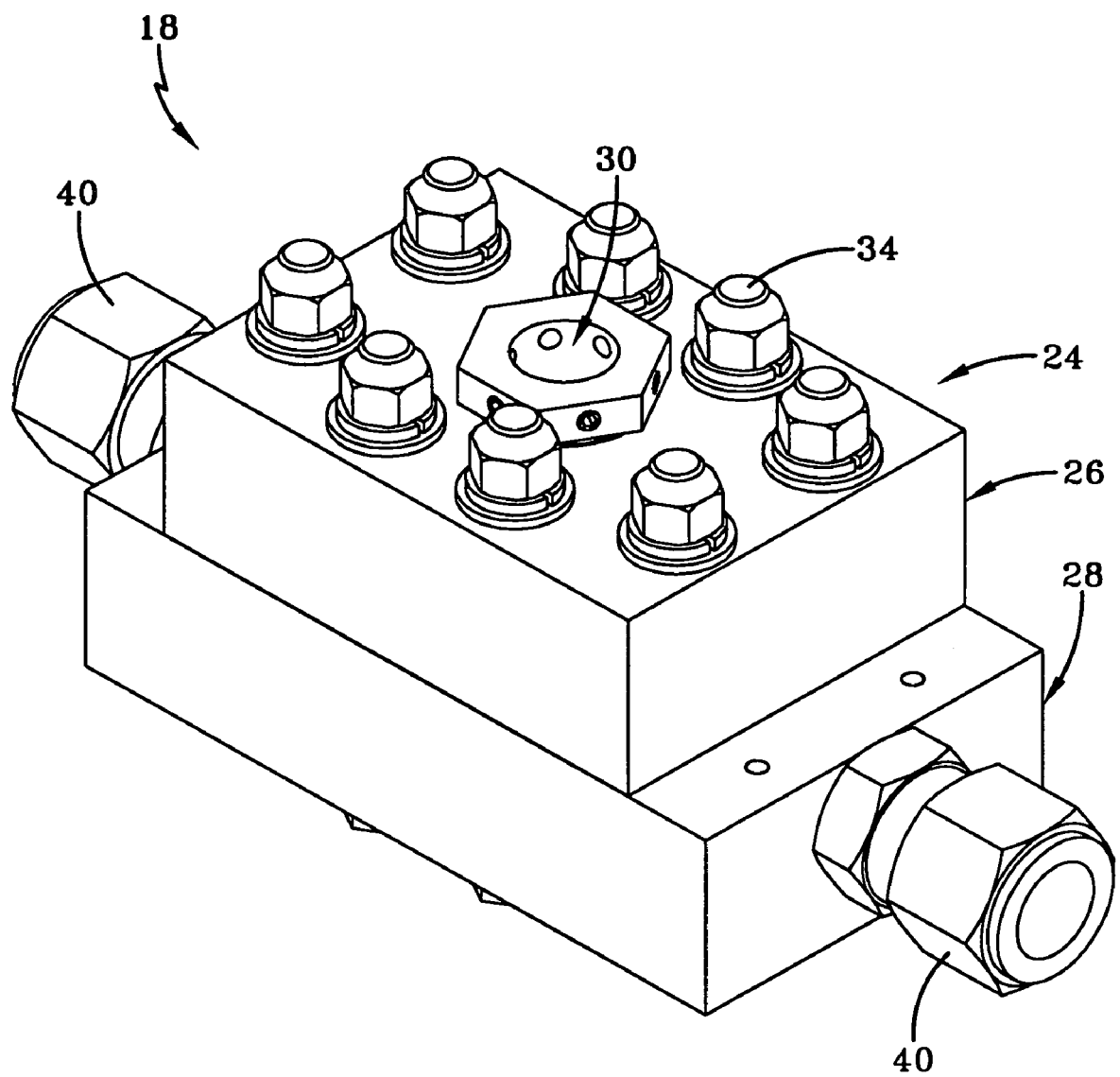
FIG. 2 is a perspective view of an optical flow cell made in accordance with the concepts of the present invention.
Figure 3:
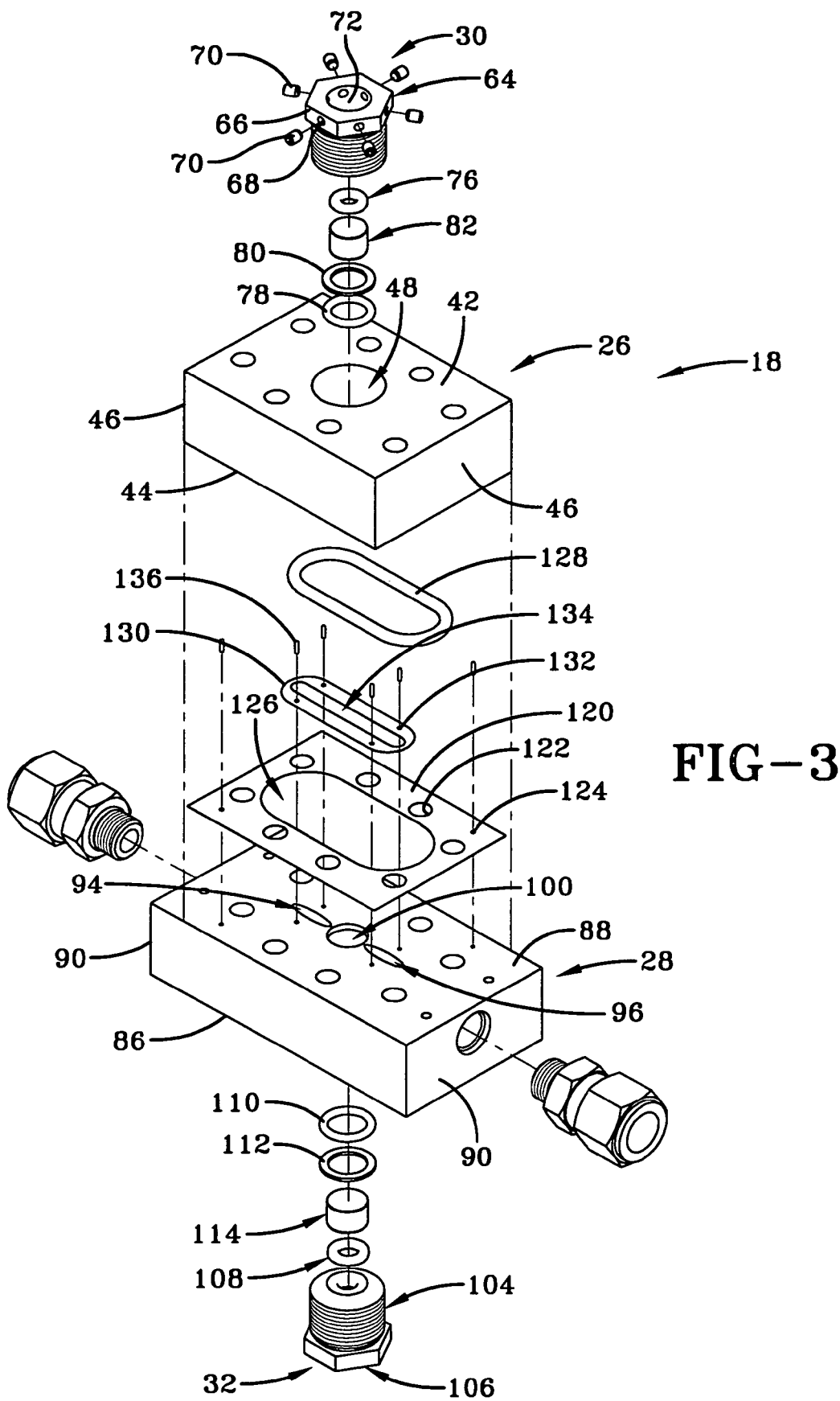
FIG. 3 is a perspective exploded view of the optical flow cell.

Referring now to FIGS. 2 and 3, it can be seen that the flow cell 18 includes a body 24. The body 24 may be composed of a cap block 26 and a base block 28. The cap block 26 provides a light entry fixture 30 through which the system's light source 16 may transmit light. The base block 28 provides an imaging fixture 32 through which the system's light detector may detect light passing through the flow cell. In a preferred embodiment, these blocks are composed of type 430 stainless steel. Each block provides one or more aligned hole fasteners 34 therethrough. The blocks are secured to one another to maintain the positioning of the apertures with respect to one another and to facilitate the flow of fluid therethrough.

The body 24 may include many other embodiments in addition to the particular embodiment in FIGS. 2 and 3. Various other embodiments may have a body made up of more than two blocks. Other embodiments may include blocks composed of other materials that may include, but are not limited to: stainless steel type 302, 304, 316, 321, 410, 420, and/or 440. Moreover, the blocks 26 and 28 may be designed such that the nuts and bolts do not protrude past the outer surface of the body. In other words, the outer surfaces of the nuts and bolts may be flush or recessed with respect to the outer surface of the body. Various other embodiments may utilize screws, rivets, epoxy, welds or other fastening means known in this and related arts. In addition, although the illustrations suggest that the blocks differ in size; other embodiments may include blocks of similar size or identical size. Moreover, the body of this concept is not limited to planar-surfaces, but may be configured in any form to which the user desires.

Figure 4:
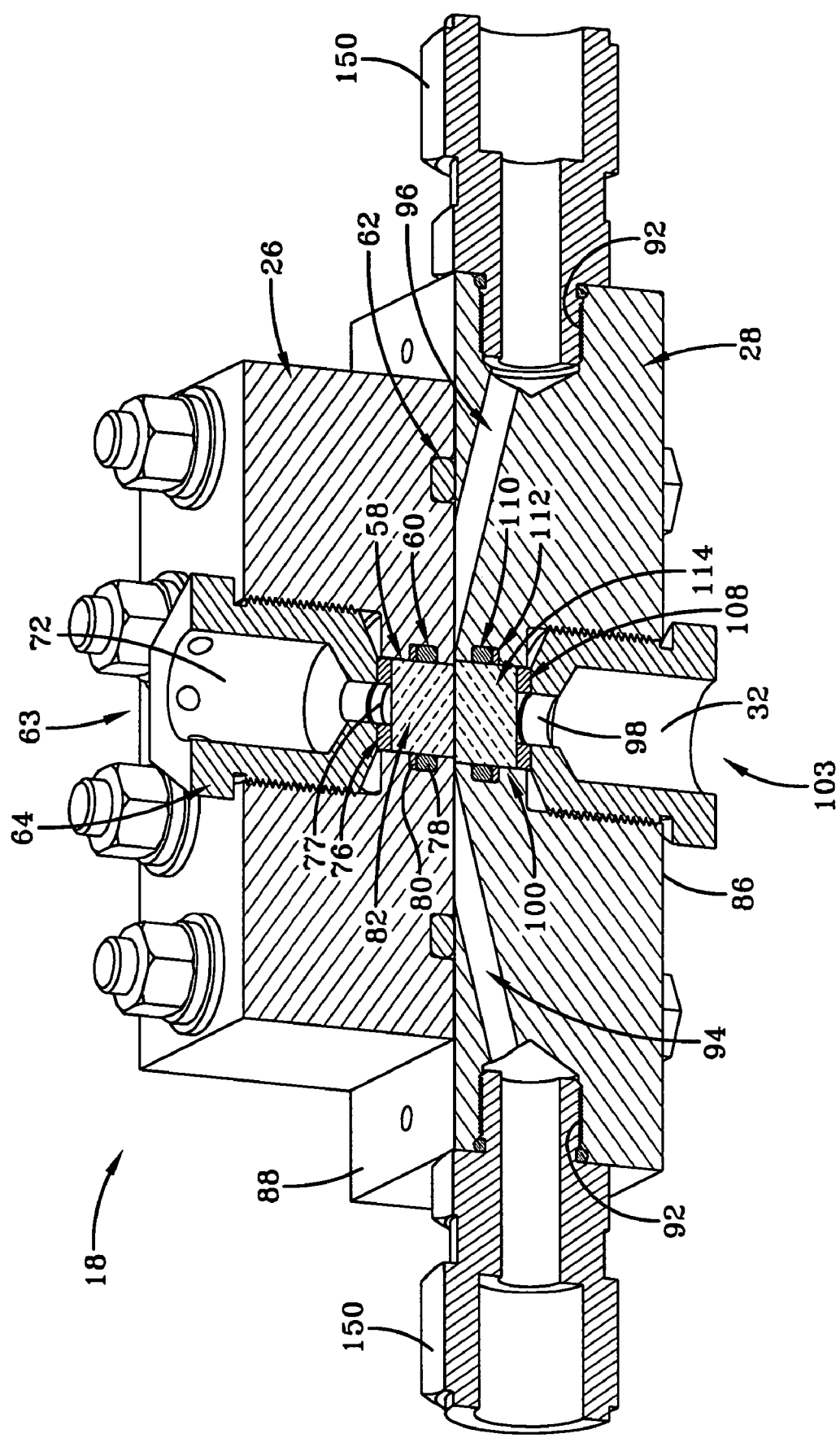
FIG. 4 is a perspective cross-sectional view of the optical flow cell.

Referring now to FIGS. 3 and 4, the cap block 26 includes an outer surface 42 opposite a facing surface 44. The surfaces 42 and 44 are each connected to one another by end surfaces 46 so as to form a substantially rectangular block. However, the shape of the cap block 26 is not critical to the operation of the optical flow cell. In any event, the cap block 26 provides a cross aperture 48, which is partially threaded, and which extends from the outer surface 42 toward the facing surface 44. A plate aperture 58 extends from the facing surface toward the outer surface 42. The apertures 48 and 58 are aligned and substantially concentric with one another wherein the plate aperture 58 has a somewhat smaller diameter than the cross aperture 48. The cap block 26 also provides a plate aperture groove 60 which is recessed into the block and disposed annularly about the plate aperture 58. The facing surface 44 provides a seal channel 62 which is disposed around the plate aperture 58.

The flow cell body 24 may receive the light entry fixture 30 that provides an opening through which the light source can direct the light. In a particular embodiment, the light entry fixture 30 may include a light entry cap 64. The light entry cap 64, which may be at least partially threaded, is received in the cross aperture 48. Various embodiments may include a light entry cap 64 that provides a cap head 66 with lateral screw holes 68 extending therethrough. The screw holes 68 receive set screws 70 which are used to tighten upon any fixture inserted into the light entry cap 64. Other various embodiments will not include screw holes 68 or set screws 70. In particular, the light entry cap 64 provides a cap opening 72 which extends therethrough. Accordingly, the light source 16 is routed into the light entry cap and retained in the cap opening by tightening the set screws 70 as needed. The fixture 30 may also include a light entry washer 76, which has a washer opening 77 extending therethrough, is inserted into the plate aperture 58 such that the opening 77 is aligned with the cap opening 72. An o-ring 78 and a backing ring 80 are received in the plate aperture groove 60. A light plate 82 is received in the plate aperture 58 and is shaped so as to allow for a press fit of the plate 82 into the aperture 58. The o-ring 78 and the backing ring 80 are positioned around the outer diameter of the light plate. The light plate is positioned such that it is adjacent to or at least abuts the light entry washer 76 at one end. The other end of the light plate 82 is positioned substantially flush with the facing surface 44.

The base block 28, which is ideally made of the same material as the cap block 26, also provides an outer surface 86 which is opposite a facing surface 88. When assembled, the blocks respective facing surfaces face or are adjacent to one another. The surfaces 86 and 88 are joined to each other by end surfaces 90. Each end surface 90 provides at least a partially threaded bore 92 which extends from the end surface inwardly. Extending further from each bore 92 is a corresponding inlet channel 94 and an outlet channel 96. As best seen in FIG. 4, the channels 94 and 96 are angularly directed so as to extend from the end of the respective bore 92 toward the facing surface 88.

The base block 28, also provides a cross-aperture 98 which extends from the outer surface 86 toward the facing surface 88. Aligned and substantially concentric with the cross-aperture 98 is a plate aperture 100 which extends from the facing surface toward the outer surface 86. The cross-aperture 98 is also partially threaded and has a somewhat larger diameter than the plate aperture 100. The block 28 also provides a plate aperture groove 102 which is recessed from the plate aperture 100 and disposed annularly about the aperture 100.

The flow cell body 24 may receive a light imaging fixture 103 that provides an opening through which the light detector can receive the light. In a particular embodiment, the light imaging fixture may include a light imaging cap 104. The light imaging cap 104, which may be partially threaded, is received in the cross-aperture 98. The light imaging cap 104 has a cap opening 106 extending therethrough and substantially aligned with the plate aperture 100. A light entry washer 108 having a washer opening 109 therethrough is received in the plate aperture 100. An o-ring 110 and a backing ring 112 are received in the plate aperture groove 102 and seal around an imaging plate 114 which is received in the plate aperture 100. The imaging plate 114 is similar in construction to the light plate 82, but has a slightly larger outer diameter so as to facilitate construction of the assembly. In any event, the plate aperture 100 may be sized and located so as to be medially positioned between the inlet channel 94 and the outlet channel 96. In other words, the channels 94, 96 exit from the facing surface 88 in close proximity to the plate aperture 100 but are not contiguous therewith. The imaging plate 114 is contained within the plate aperture 100 by a press fit and the one end of the imaging plate is substantially flush with the facing surface 88. The other end of the imaging plate 114 is placed adjacent to or abuts the light entry washer 108 which in turn is adjacent to or abuts the light imaging cap 104.

Figure 7:
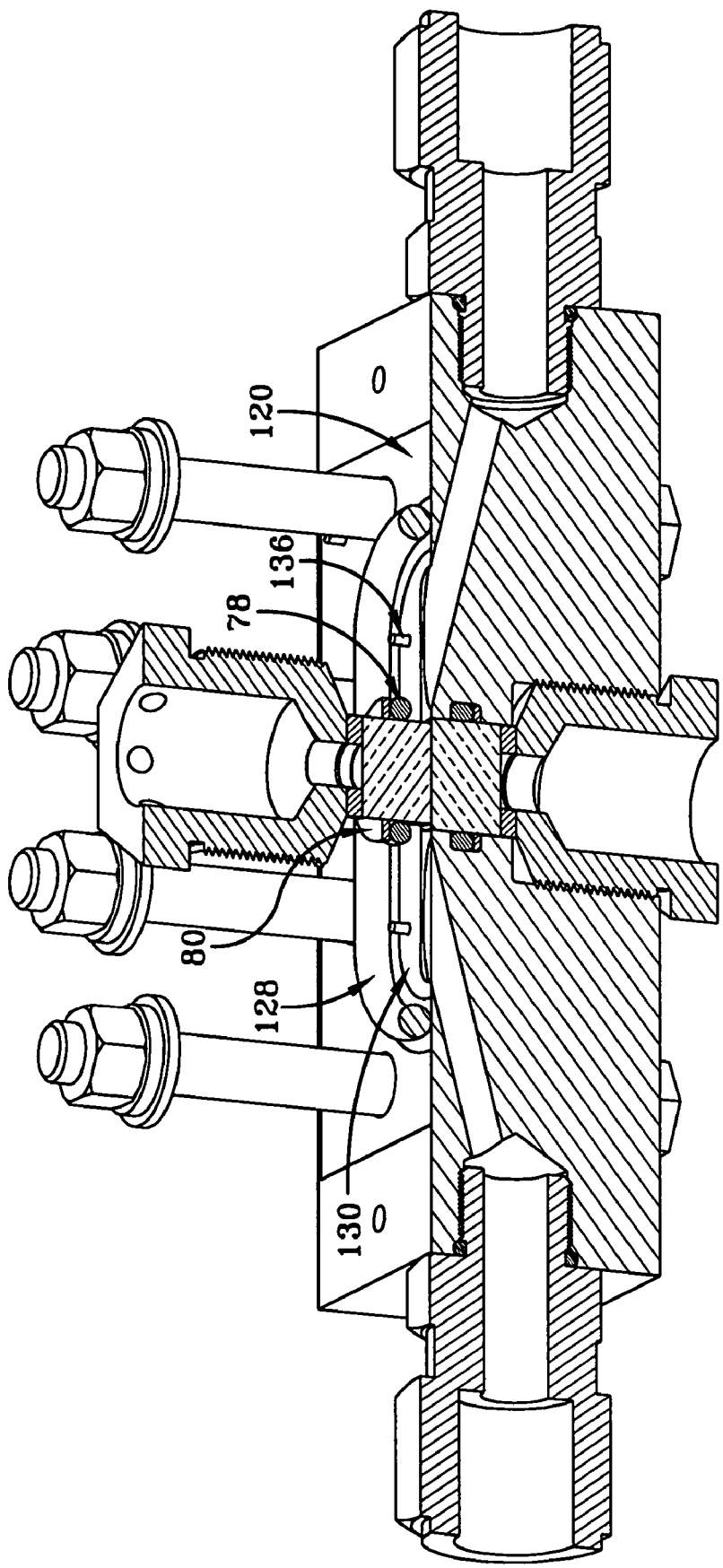
FIG. 7 is a perspective cross-sectional view of the optical flow cell to show internal components more clearly.

Referring now to FIGS. 3 and 7, it can be seen that a series of components are interposed between the cap block 26 and the base block 28 so as to allow for a flow of fluid between the blocks as delivered by the flow delivery apparatus 20. In particular, the flow cell 18 includes an outer shim 120 which has a thickness of about 100 microns, and which has a plurality of fastener openings 122 which allow the fasteners 34 to extend between and through the blocks 26 and 28. The shim 120 also provides one or more alignment openings 124 as well as a major opening 126. The major opening 126 is sized to surround the seal channel 62 and, as shown, is substantially oval in shape. The major opening 126 also effectively surrounds the channels as they exit from the facing surface and the apertures provided by both of the blocks 26 and 28. An oval seal 128 is made from a polymeric material and is received in the seal channel 62. The seal 128, with the blocks 26 and 28 secured to one another assists in keeping the fluid being inspected from flowing in a manner other than through a flow opening as will be discussed.

Figure 6:
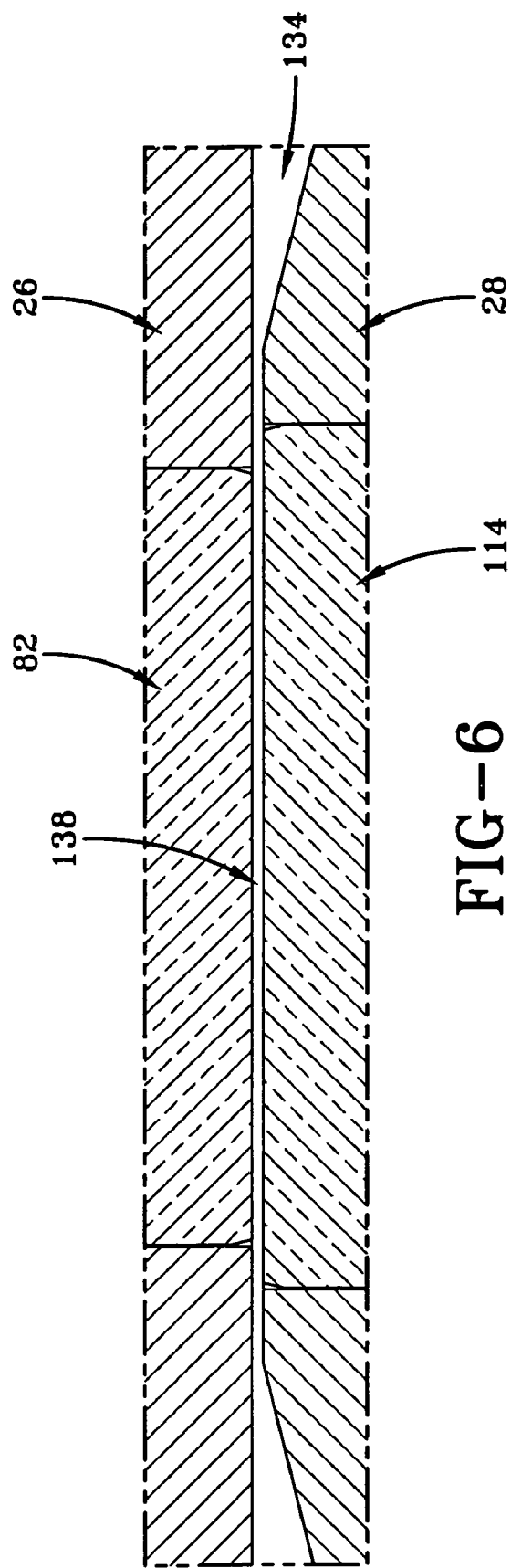
FIG. 6 is an enlarged cross-sectional view of a flow channel provided by the optical flow cell.

An inner shim 130, which has substantially the same thickness as the outer shim 120, provides one or more alignment openings 132 extending therethrough. The inner shim 130 provides a flow opening 134 wherein the inner shim 130 is sized to fit within the oval seal 128 and the flow opening 134 is sized to be contiguous with the inlet and outlet channels 94, 96 and also positioned about the plates 82 and 114. One or more alignment pins 136 are received in corresponding holes provided by the blocks 26 and 28 and extend through the outer shim 120 and the inner shim 130. The alignment pins are used to maintain proper positioning of the shims in relation to the channels and to ensure that the flow opening 134 is aligned with the channels and plate apertures. When the blocks are assembled to one another, and the various washers and plates are positioned within the respective blocks, and the fasteners secure the blocks to one another a flow channel 138 is formed between the plates 82 and 114. In particular, as best seen in FIG. 6, the flow channel 138 is further defined by the flow opening 134. The flow channel 138 transitions the flow fluid received through the inlet channel, and subsequently forms the fluid into a laminar flow such that the light detector and analysis device can function as they are intended. The flow of fluid then exits the outlet channel from the flow channel 138 and returns to the operational mechanism which is being monitored.

Figure 8:
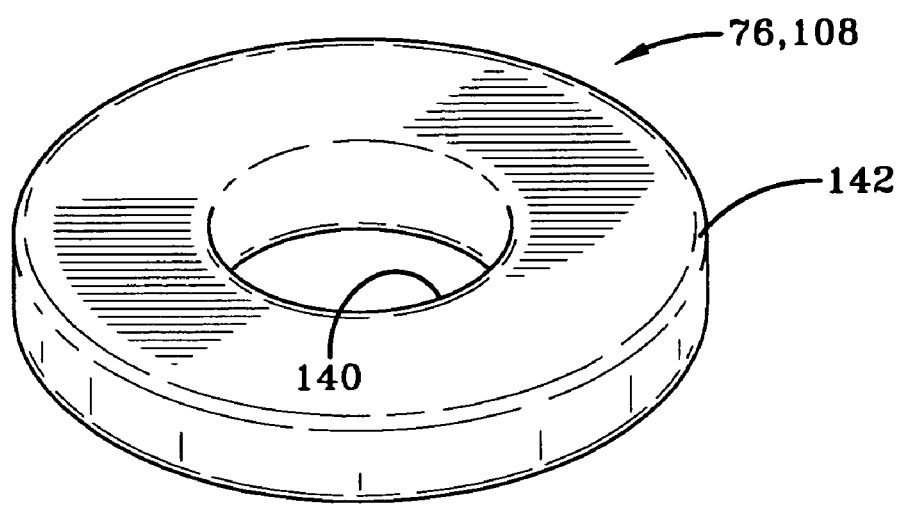
FIG. 8 is a perspective view of a washer used in the optical flow cell.
Figure 9:
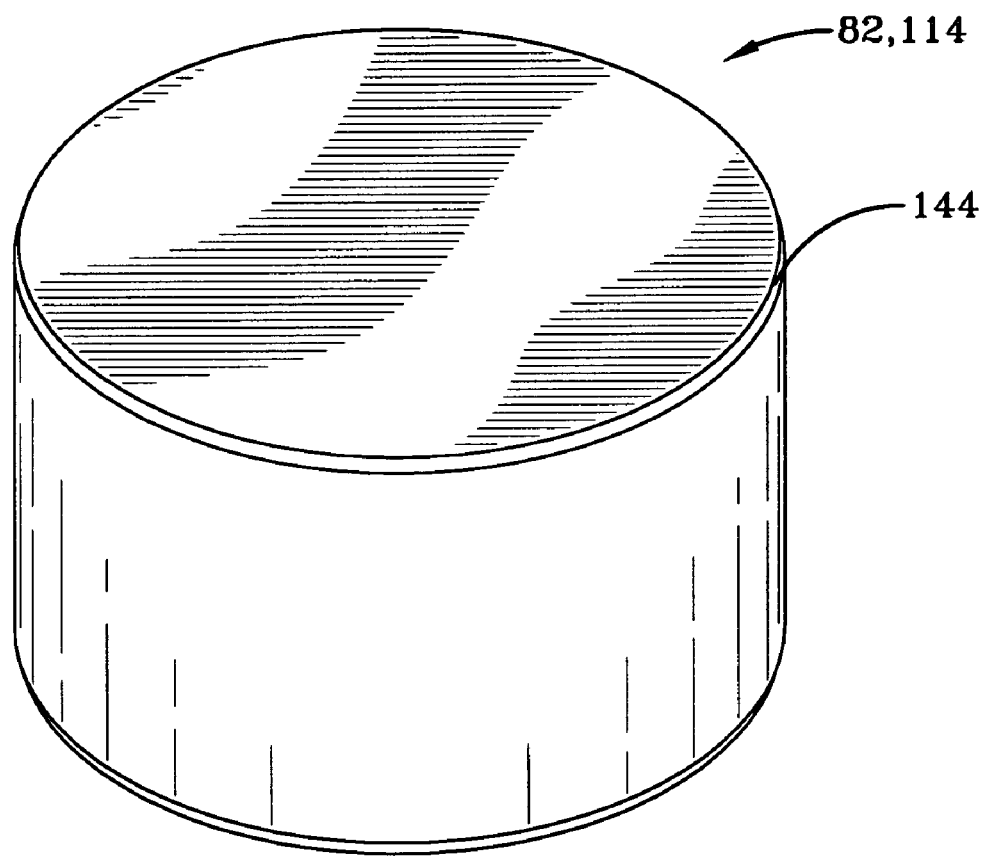
FIG. 9 is a perspective view of a plate used in the optical flow cell.

Referring now to FIGS. 8 and 9, modifications are made to the plates and washers to allow the flow cell to withstand the temperature and pressure that the fluid exerts in the flow channel 138. In particular, the washers 76 and 108 provide interior chamfered edges 140 and external chamfered edges 142. In a similar manner, the plates 82 and 114 may provide chamfered edges 144. Use of the chamfers on the washers and the plates distributes the forces or loads generated by the pressurized fluid flowing through the channel 138. Unchamfered edges tend to increase pressure points and cause the plates and/or washers to break thereby destroying the integrity of the flow cell.

Attached to each end of the block 28 is a coupling 150 that is threadingly received into each threaded bore 92. Each coupling 150 is connected to the flow delivery apparatus 20. The present concept is not limited to the couplings 150 shown, but may include any other connection device used in this and similar arts. Various embodiments may not use a coupling at all. Moreover, the present concept includes alternative arrangements of the channels 94, 96 so long as laminar flow exists in critical regions between the channels. For example, while the drawings show both channels 94, 96 existing in the cap block 28, this concept includes other embodiments in which both channels 94, 96 exist in the base block 26. And this concept also includes embodiments where one channel exists in one block and the other channel exists in the other block. Furthermore, the channels need not be on opposite sides of the flow cell. For example, alternative embodiments include those in which the inflow and outflow channels may exist on the same side of the blocks, and also include those embodiments where the channels exist at right angles (or any other angle) to one another.

The flow cell 18 is configured for high pressure and high temperature applications. At these temperatures and pressures, steep gradients in pressure over an area (i.e., large forces) can cause internal damage to a part. Accordingly, one particular triumph of the current concept lies in its method of vertical assembly as shown in FIGS. 3 and 4, which tends to minimize such large internal forces. Thus, one advantage of the flow cell 18 is that large internal forces are minimized. More specifically, the flow cell minimizes large forces acting on the two plates. Two major sources of stress often exist: high temperatures causing thermal expansion, and high-pressure oil exerting force on the light entry plate 82 and the imaging plate 114. For example, consider an embodiment where the plates are made of glass. Glass is brittle, meaning that is does not flex an appreciable amount. To keep glass from fracturing, a preferred embodiment may choose the materials of the flow cell (gaskets, glass, aluminum washer, stainless steels) to match the coefficients of thermal expansion over a possible 140° C. range at a maximum pressure (5000 psi). In other words, the coefficients of thermal expansion for the fixtures 30 and 32, which may at least include their respective caps, washers, o-rings, backing rings and plates, are equated to the coefficients of thermal expansion for their associated blocks 26 and 28. Accordingly, when the temperature of the flow cell rises as the potentially high temperature fluid passes therethrough, the dimensional integrity of the flow channel 138 is maintained. Use of the chamfered washers and plates also maintains the flow channel's integrity. As a result, the imaging of the debris contained in the fluid is not adversely affected.

Figure 5:
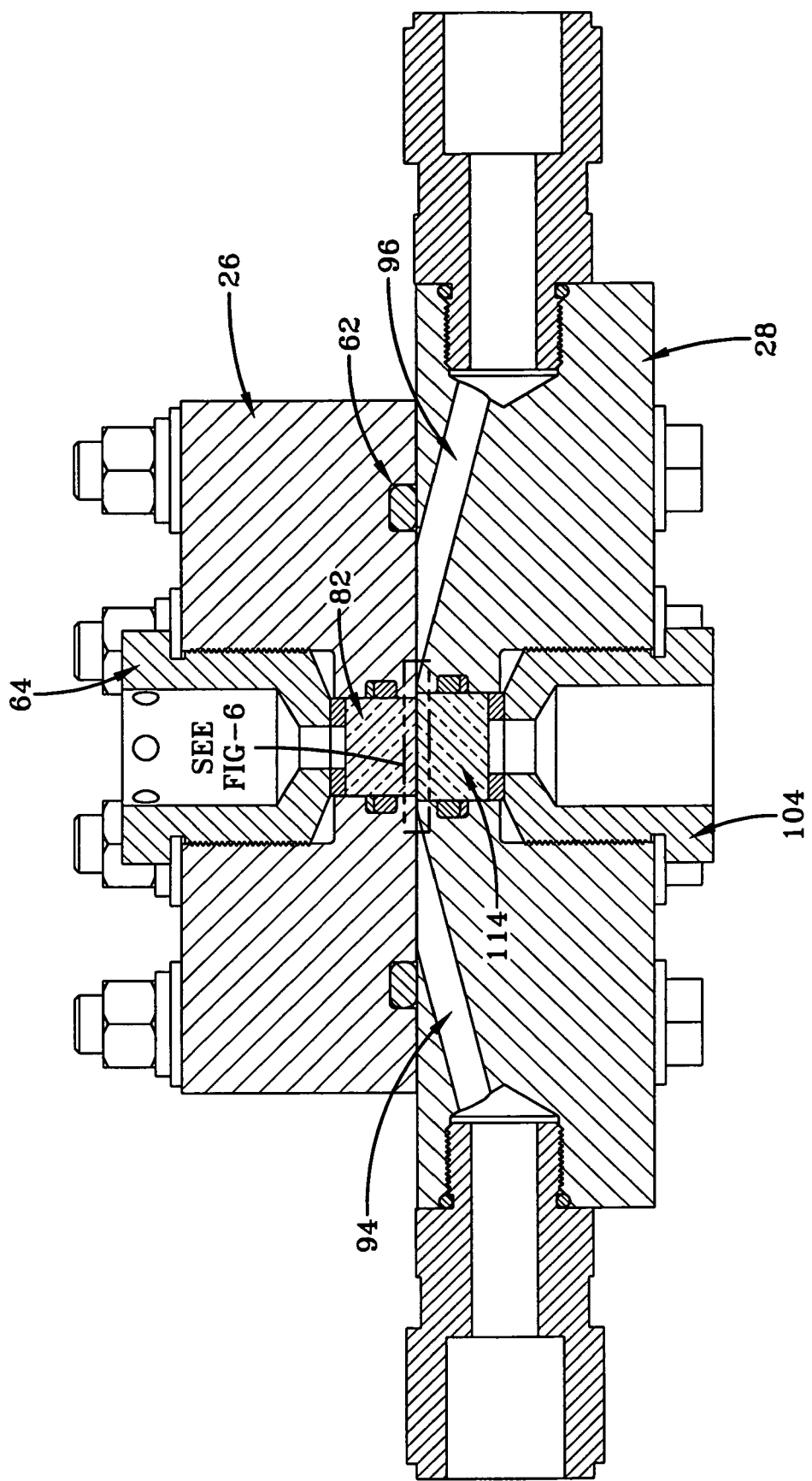
FIG. 5 is an elevational cross-sectional view of the optical flow cell.

As shown in FIGS. 5 and 6, a viewing region is located largely between the light entry plate 82 and the imaging plate 114. A particular challenge in this region dealt with keeping the viewing region's depth constant over a wide range of temperatures and at high pressure. Ideally, the depth of this viewing region is 105 μm plus-or-minus 5 μm. This depth allows for the system to image typical particles, often of about 100 μm or less in size.

Other embodiments of the present concept may include flow cells having only an inner shim, only an outer shim, or no shims at all. Furthermore, the shape of any shims utilized is not limited to the shape of the shims in FIG. 7, but rather may extend to any shape that a person skilled in the art might utilize. Moreover, the shims are not limited to stainless steel, but may be composed of any substance that aids in meeting the high pressure and high temperature demands of the current part. Moreover, if shims are utilized, they are designed in light of the thermal expansion coefficients of any components of a vertical assembly as discussed above.

High-pressure fluid may pass through the viewing region (see FIGS. 5 and 6). Some common examples of a high-pressure fluid are lubricating oil (typically having a pressure of approximately 200 psi) and hydraulic oil (often having a pressure of about 5000 psi). When a high-pressure fluid passes through the viewing region, it presents several challenges. First, the fluid exerts pressure against the light entry plate 82 and the imaging plate 114. Accordingly, these plates must be constructed so as to resist this high pressure oil.

The flow cell disclosed herein withstands the added stress experienced by parts at high temperatures and pressures. More particularly, over a wide temperature range and at high pressure, such a flow cell may maintain a relatively constant viewing region and maintain laminar flow across that viewing region. The materials of the flow cell (gaskets, glass, stainless steels, etc.) are chosen so that the coefficients of thermal expansion minimize internal stresses on the part over a temperature range of 140° C. and at a pressure of 5000 psi.

The present invention has a much wider scope of application than mere incorporation into automotive engines. For example, in the aircraft industry, predicting failure is critically important to avoid accidents and loss of life. Thus, system designers in the art would greatly benefit from the present invention. Most notably, these designers could use such a system in engines, hydraulic systems for brakes and landing gear, and many other parts of an airplane through which liquids pass. Furthermore, the present invention can be used with fluids other than engine oil. Indeed, other monitored fluids might include (but are not limited to) lubricating oils; hydraulic fluids; fluids used in industrial quality control, food processing, medical analysis, and environment control; as well as numerous others.

Accordingly, one advantage of the optical flow cell 18 is to maintain a relatively constant depth of fluid between the two optically transparent plates over a wide range of temperatures and pressures. In particular, the present concept strives to keep uniform laminar flow between the two optically transparent plates. Moreover, another advantage is to provide a flow cell that could be monitored over a network. For example, in oil rigs, windmills, or other systems that may be in remote locations and require relatively little maintenance, it may be useful to remotely monitor the fluids in the system and send a repairman only when maintenance is required. In addition, the repairman should already know the nature of the problem, and as such will only need limited equipment and limited time. Because "time is money," the present concept will also offer reduced costs for final maintenance.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto and thereby. Accordingly, for an appreciation of the true scope and breadth of the invention, reference should be made to the following claims.

The invention claimed is:

1. An optical flow cell comprising:
   a flow cell body having an inlet and an outlet, said flow cell body comprising a base block and a cap block that are coupled together;
   an inner shim and an outer shim positioned between said base block and said cap block, wherein said outer shim is concentrically disposed outside said inner shim, said inner shim forming a flow opening between said base block and said cap block to allow fluid to pass between said inlet and said outlet;
   a seal located between said inner shim and said outer shim; and
   a light entry fixture and a light imaging fixture carried by said flow cell body, said light entry fixture positioned at one side of said flow opening and said light imaging fixture positioned at an opposite side of said flow opening.

2. The optical flow cell according to claim 1, wherein said fixtures are made from at least some materials different than said flow cell body but having said thermal expansion rate so as to maintain a predetermined size of said flow opening.

3. The optical flow cell according to claim 1, wherein said inlet and outlet fluidly communicate with at least a portion of said flow opening.

4. The optical flow cell according to claim 3, further comprising:
   couplings received in one of said blocks and linked to said inlet and said outlet.

5. The optical flow cell according to claim 4, wherein said inlet and said outlet are in one of said blocks, and wherein said inlet and said outlet are angled into said flow opening.

6. The optical flow cell according to claim 1, wherein said light entry fixture is at least partially threaded and includes a cap opening which extends therethrough and a cap head with lateral screw holes extending therethrough, wherein said light imaging fixture is at least partially threaded and includes a cap opening which extends therethrough, and wherein said base block includes a cross aperture which is partially threaded and a plate aperture which is aligned with said cross aperture and is smaller than said cross aperture.

7. The optical flow cell according to claim 6, further comprising:
   a light plate received in said plate aperture, wherein said light plate has chamfered edges.

8. The optical flow cell of claim 7, wherein said base block provides
   a recessed groove annularly disposed about said plate aperture;
   a backing ring, positioned in said recessed groove; and
   an o-ring positioned in said recessed groove, said backing ring and said o-ring disposed about said light plate.

9. The optical flow cell of claim 6, further comprising:
   a light imaging cap with a head, wherein said light imaging cap is at least partially threaded; and
   a light entry cap with a head, wherein said light entry cap is at least partially threaded.

10. The optical flow cell of claim 1, further comprising:
    at least one fastener that holds said base block and said cap block together.

\* \* \* \* \*